US005391163A

United States Patent [19]

Christine et al.

[11] Patent Number: 5,391,163

[45] Date of Patent: Feb. 21, 1995

[54] POUCH FOR ADMINISTERING MEDICAL FLUIDS

[75] Inventors: William C. Christine; Peter G. DeRaymond, both of Nazareth, Pa.

[73] Assignee: Inpaco Corporation, Nazareth, Pa.

[21] Appl. No.: 829,846

[22] Filed: Jan. 31, 1992

[51] Int. Cl.[6] ........ A61M 5/00

[52] U.S. Cl. ........ 604/408; 604/403; 604/411

[58] Field of Search ........ 604/403, 408, 411, 415, 604/262, 317, 322; 206/438

[56] References Cited

U.S. PATENT DOCUMENTS

| | | | |
|---|---|---|---|
| 1,581,072 | 4/1926 | Lumsden . | |
| 2,693,189 | 11/1954 | Ryan | 128/282 |
| 2,698,619 | 1/1955 | Beacham et al. | 128/272 |
| 2,853,069 | 9/1958 | Beacham et al. | 128/214 |
| 2,989,053 | 6/1961 | Hamilton | 128/221 |
| 3,313,472 | 4/1967 | Tjerneld et al. | 229/62.5 |
| 3,376,687 | 4/1968 | Gewecke | 53/14 |
| 3,416,528 | 12/1968 | Kahn | 128/214.2 |
| 3,583,460 | 6/1971 | Faust | 150/8 |
| 3,598,150 | 8/1971 | Nolan | 137/625.32 |
| 3,610,297 | 10/1971 | Raaf et al. . | |
| 3,648,697 | 3/1972 | Gardner | 128/272 |
| 3,724,461 | 4/1973 | Eisenberg | 128/227 |
| 3,778,369 | 12/1973 | Markley | 210/321 |
| 3,894,381 | 7/1975 | Christine et al. | 53/128 |
| 3,915,212 | 10/1975 | Bujan et al. | 150/8 |
| 3,976,073 | 8/1976 | Quick et al. | 128/272 |
| 3,991,912 | 11/1976 | Soto | 222/89 |
| 4,010,786 | 3/1977 | Aguettant et al. . | |
| 4,183,434 | 1/1980 | Watt | 206/438 |
| 4,187,893 | 2/1980 | Bujan | 150/8 |
| 4,188,989 | 2/1980 | Andersen | 150/9 |
| 4,234,026 | 11/1980 | Bayham | 150/8 |
| 4,235,233 | 11/1980 | Mouwen | 128/214 |
| 4,246,062 | 1/1981 | Christine | 156/498 |
| 4,270,533 | 6/1981 | Andreas | 128/214 F |
| 4,278,198 | 7/1981 | Norton et al. | 229/55 |
| 4,280,498 | 7/1981 | Jensen | 128/283 |
| 4,338,933 | 7/1982 | Bayard et al. | 128/214 R |
| 4,346,820 | 8/1982 | Cavazza | 222/83 |
| 4,364,387 | 12/1982 | Larkin | 128/214 C |
| 4,365,629 | 12/1982 | Pert et al. | 604/408 |
| 4,381,776 | 5/1983 | Latham, Jr. | 604/317 |
| 4,432,759 | 2/1984 | Gross et al. | 604/411 |
| 4,432,765 | 2/1984 | Oscarsson | 604/411 |
| 4,443,219 | 4/1984 | Meisch et al. | 604/317 |
| 4,463,862 | 8/1984 | Hansen | 215/33 |
| 4,465,487 | 8/1984 | Nakamura et al. | 604/408 |
| 4,469,249 | 9/1984 | Malpas et al. | 222/83 |
| 4,484,351 | 11/1984 | de Leeuwe et al. | 383/9 |
| 4,512,136 | 4/1985 | Christine | 53/410 |
| 4,534,758 | 8/1985 | Akers et al. | 604/85 |
| 4,535,758 | 8/1985 | Longacre, Jr. | 128/6 |
| 4,547,900 | 10/1985 | Larkin et al. | 383/5 |
| 4,548,606 | 10/1985 | Larkin . | |
| 4,553,971 | 11/1985 | Ashley et al. | 604/415 |
| 4,586,928 | 5/1986 | Barnes et al. | 604/408 |
| 4,596,571 | 6/1986 | Bellotti et al. | 604/411 |
| 4,629,080 | 12/1986 | Carveth | 215/11 R |
| 4,637,934 | 1/1987 | White | 426/117 |
| 4,675,019 | 6/1987 | Bellhouse et al. | 604/408 |
| 4,676,775 | 6/1987 | Zolnierczyk et al. | 604/28 |
| 4,722,727 | 2/1988 | Ogden et al. | 604/29 |
| 4,723,956 | 2/1988 | Schnell et al. | 604/414 |
| 4,794,750 | 1/1989 | Schmidt et al. | 53/410 |
| 4,838,875 | 6/1989 | Somor | 604/262 |
| 4,854,737 | 8/1989 | Steer et al. | 383/127 |
| 4,981,374 | 1/1991 | Rutter et al. | 383/37 |
| 5,084,041 | 1/1992 | Oxley et al. | 604/408 X |

FOREIGN PATENT DOCUMENTS

| | | | |
|---|---|---|---|
| 2016523 | 5/1970 | France . | |
| 2225351 | 11/1974 | France . | |
| 2104044 | 3/1983 | United Kingdom | 604/408 |

*Primary Examiner*—Sam Rimell

*Attorney, Agent, or Firm*—Seidel, Gonda, Lavorgna & Monaco

[57] ABSTRACT

A pouch and coupler which is used for administering medical products includes a fluid reservoir section and a sterile section, with the coupler positioned within the sterile section. The reservoir being sealed such that the fluid cannot pass through the coupler. The coupler including a projection which extends through a seal into the reservoir so as to provide access through the coupler. The sterile section being openable to provide access to the coupler and provide a passage from the reservoir through the coupler to an administration set. In an alternative embodiment, the coupler includes a projecting poppet which extends through the coupler so as to provide the fluid access.

19 Claims, 5 Drawing Sheets

FIG. 9
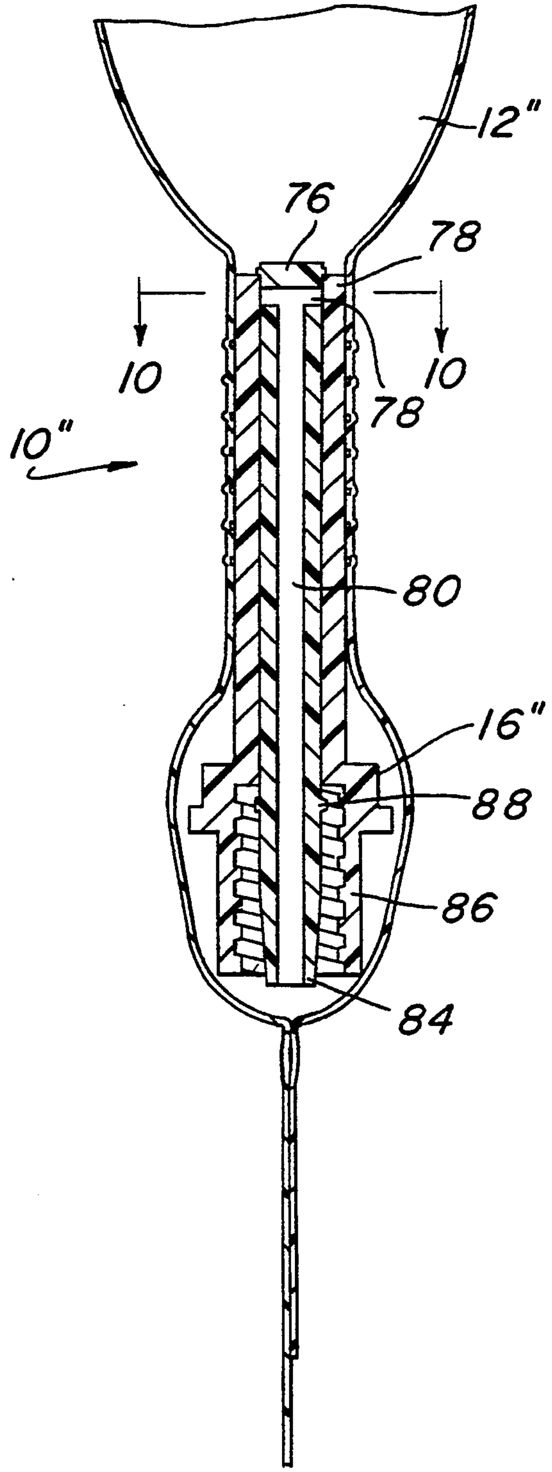
FIG. 12
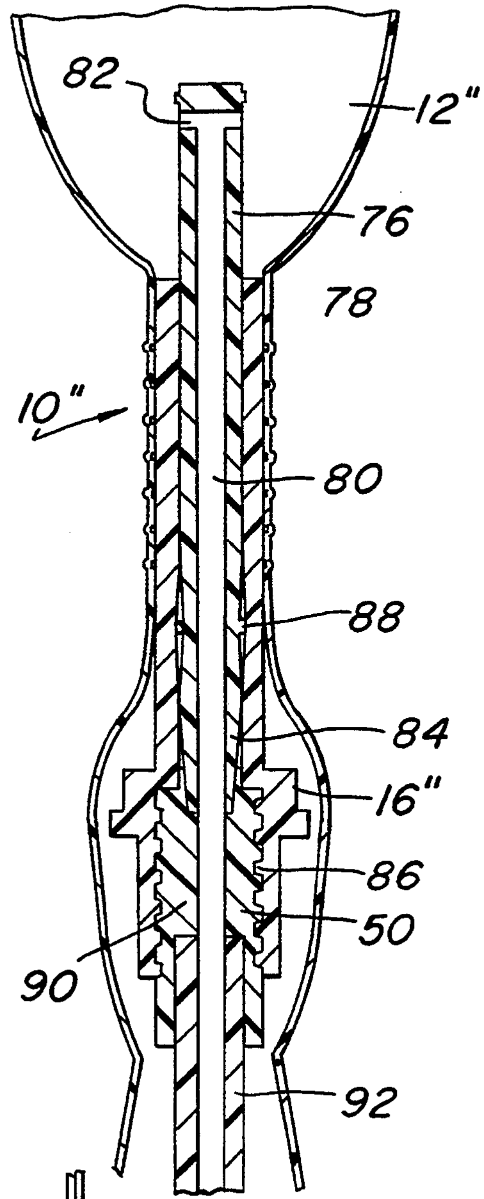
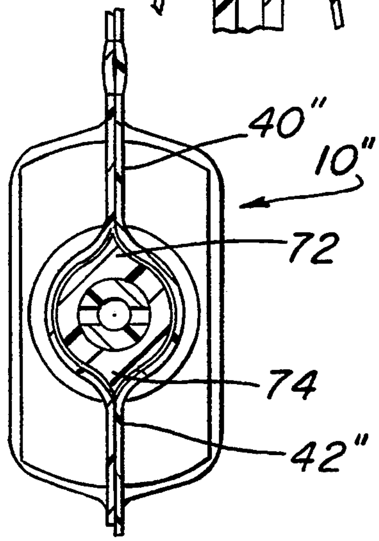
FIG. 10

POUCH FOR ADMINISTERING MEDICAL FLUIDS

FIELD OF THE INVENTION

The present invention relates to a pouch of the type used for retaining fluids, such as medical fluids for purposes of administration. The present invention includes an attachment structure for connecting with a fluid administration set and for transferring the liquid from within the pouch. The present invention may also include a coupler which is actuated by the attachment to the administration set. The present invention may also be used to accomplish the connection between the pouch and the administration set in a sterile manner.

BACKGROUND OF THE INVENTION

Medical fluids are often supplied to living organisms through an administration set which is connected to a source of the fluid through flexible tubing. Medical fluids are administered parenterally and enterally.

The source of the various types of medical fluids typically includes a reservoir or the like having a tap which is mounted at the bottom end thereof such that when the reservoir is hung above the patient, a substantially constant supply and pressure is provided to the patient.

Previously, reservoir units were made of glass and required sterilization. More recently, medical fluids have been prepared in advance and provided in sterile flexible pouches which are sealed during filling. Such pouches may be of the type which are prepared in a continuous automatic form/fill/seal machine such as those manufactured by Inpaco Corporation of Nazareth, Pa.

In order to provide the connection between the sealed reservoir within the pouch and the intravenous syringe maintained within the patient's arm, a connection must be provided. It is contemplated that this connection must be maintained sterile. The combination of a fluid administration pouch and a sterile interconnection with a medical fluid administration set is a portion of the subject matter of the present invention.

BRIEF DESCRIPTION OF THE INVENTION

The present invention relates to a pouch and coupler of the type used for retaining and administering fluids. The pouch comprises a fluid reservoir section and a sterile section. The pouch preferably narrows at its lower end to form a channel. A coupler is sealed within the channel, forming the beginning of a sterile section. The lower portion of the sterile section encloses the lower portion of the coupler behind a peelable heat seal.

The coupler portion of the present invention may be embodied in a number of forms. In one form, the coupler includes a hollow upper portion which is retained in the sterile section. One end of the coupler includes a projection having an opening therein for extension through the narrow channel and into the reservoir section. A peelable seal is formed at the end of the channel and at the opening into the reservoir. The peelable seal encloses the projected end of the coupler within the channel and the fluid is sealed within the reservoir prior to penetration of the projected end of the coupler through the peelable seal into the reservoir.

The projected end of the coupler is exposed by opening the peelable heat seals within the sterile section. The projected end of the coupler may include means for retaining the coupler end within the reservoir section after insertion through the peelable seal or the like so that the medical fluid bag may not be reused. The projection of the one end into the reservoir may be caused by the attachment of the fluid administration set onto the opposite end of the coupler.

In another embodiment of the present invention, the coupler includes a movable poppet therein. The poppet includes a closed upper end and a channel connecting through the side wall near the closed end to a hollow portion within the poppet. The closed end of the poppet is originally located within the hollow of the coupler. The upper end of the poppet forms a seal with the coupler and thus prevents passage of fluids from the reservoir prior to the pouch's use. The poppet is slidably movable within the hollow of the coupler. The open end of the poppet projects into a hollow threaded lower end of the coupler. When the pouch is to be used, a conventional administration set is coupled to the coupler by opening the sterile section above the pouch via the peelable seals. One end of the administration set is screwed into the lower portion of the coupler immediately forming a hermetic seal therewith. As the administration set is inserted further into the coupler, the poppet rises out of the coupler and into the reservoir. The channel at the top of the poppet is exposed and forms a fluid communication between the hollow of the poppet and the administration set.

The relationship between the coupler and the sterile section of the pouch of each of the embodiments of the invention is contemplated to be such that the connection of the administration set with the couple can be made while maintaining the fluid contacting parts in a sterile condition.

For purposes of illustrating the invention, there is shown in the drawings forms which are presently preferred; it being understood, however, that this invention is not limited to the precise arrangements and instrumentalities shown.

BRIEF DESCRIPTION OF THE DRAWINGS

FIG. 9 shows a partial cross-sectional view of the pouch and coupler assembly as shown in FIG. 8.

FIG. 10 is a cross-sectional view of the pouch and coupler assembly as taken along line 10—10 in FIG. 9.

FIG. 12 is a partial cross-sectional view of the pouch and coupler assembly as taken along line 12—12 of FIG. 11.

DETAILED DESCRIPTION OF THE DRAWINGS

Figure 1:
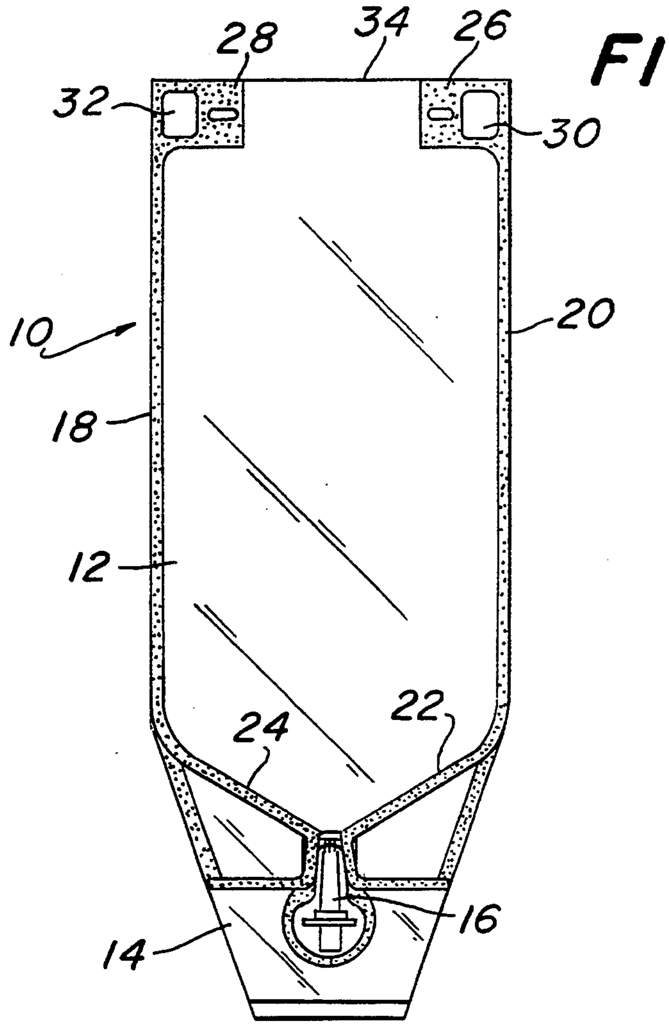
FIG. 1 shows a front plan view of a first embodiment of a pouch and coupler assembly as contemplated by the present invention.

In the drawings where like numerals indicate like elements, there is shown a pouch for purposes of administering medical products or the like. The pouch as illustrated in FIGS. 1-5 is generally indicated by the numeral 10. The pouch 10 includes a reservoir 12, a sterile section 14 and a coupler 16. The reservoir section is formed by a continuous fused heat seal between two portions of flexible plastic. The reservoir 12 is defined by the opposite side heat seals 18 and 20. At the bottom of the reservoir is provided a narrowing section formed by angled seals 22 and 24. At the top of the pouch are provided two fused portions 26 and 28 having openings therein 30 and 32, respectively. The openings 30, 32 are provided for purposes of hanging the pouch 10 such that the sterile section 14, coupler 16 and angled heat seal portions 22, 24 are positioned vertically below the reservoir section 12. The top seam 34 of the pouch 10 as illustrated as FIG. 1 is provided without a seal. In this form, the pouch 10 may be used for any fluid as desired by filling same and sealing the top edge 34. However, the pouch may also be provided pre-filled with the top seam 34 being sealed as part of its assembly. Such assembly may be performed in a continuous form/fill/seal machine as manufactured and sold by Inpaco Corporation of Nazareth, Pa.

Figure 2:
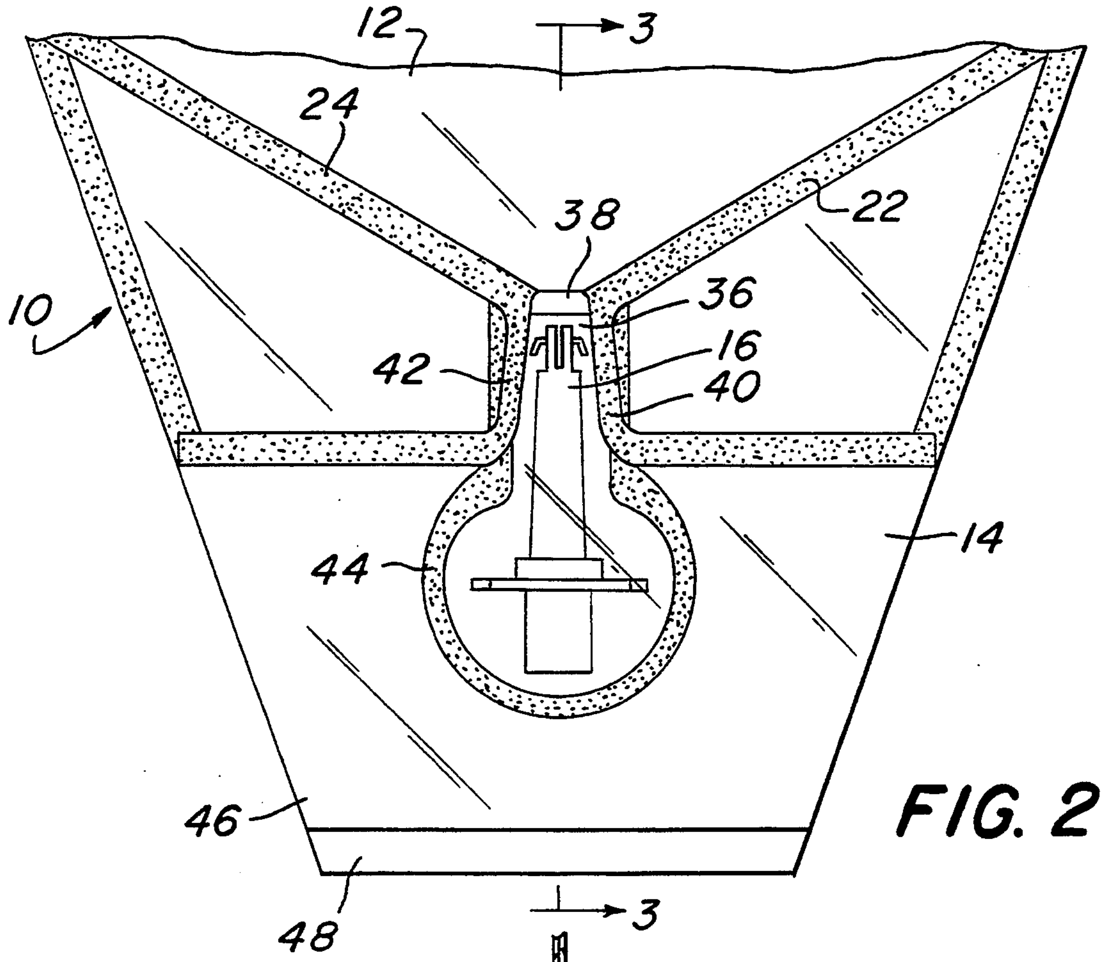
FIG. 2 shows an enlarged view of a portion of the pouch and coupler as shown in FIG. 1.

FIG. 2 shows an enlarged view of the bottom of reservoir 12, the sterile section 14 and the coupler 16. The bottom of the reservoir 12 is defined by the angled heat seals 22 and 24, respectively. Between the angled heat seals 22, 24 is provided a narrow channel 36 in which the coupler 16 is placed. Between the angled heat seals 22, 24 and the top of the narrow channel 36 is provided a peelable seal 38. The formation of fused heat seals and peelable heat seals is general known in the art.

Figure 3:
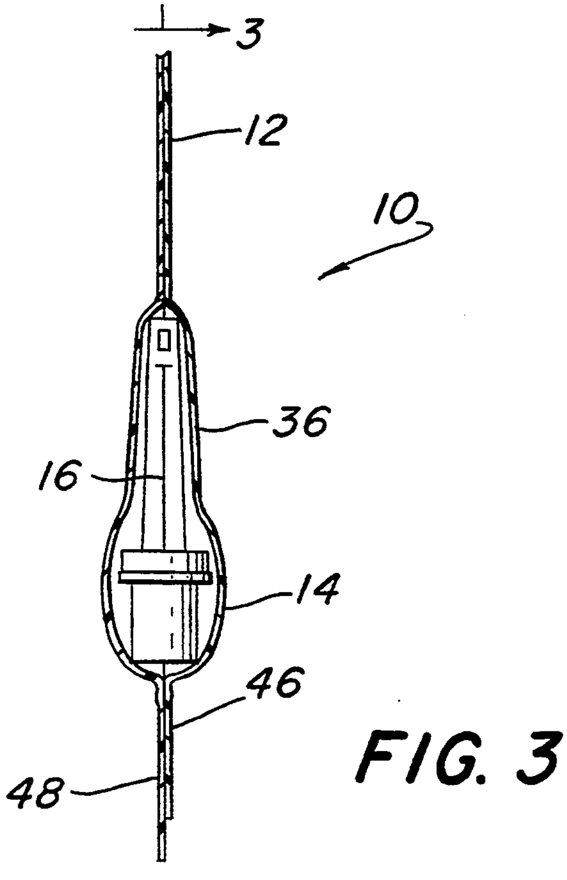
FIG. 3 shows a cross-sectional view of the portion of the pouch and coupler as taken along line 3—3 in FIG. 2.

The narrow channel 36 is defined by seals 40 and 42 on opposite sides thereof. The sterile section 14 provided at the bottom of narrow channel 36 is defined by a circular peelable seal 44 which surrounds the bottom end of coupler 16. As illustrated in FIGS. 2 and 3, the combination of peelable seal 38, opposite side seals 40, 42 and circular peelable seal 44 encapsulate the coupler 16 within the narrow channel and form the sterile section 14 of the pouch 10. The opposite sides of the pouch 10 adjacent the sterile section 14 include projecting tabs 46 and 48 which may separated so as to peal open the circular seal 44 and provide access to the coupler 16.

Figure 4:
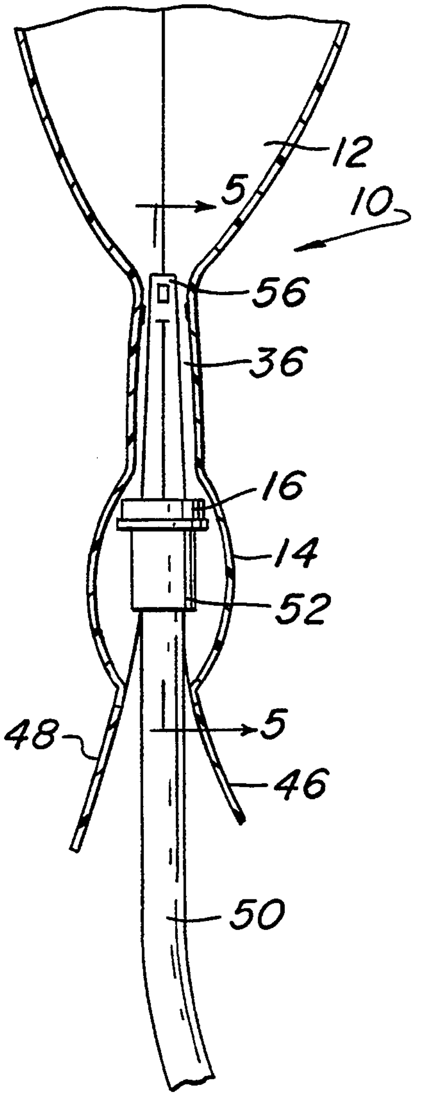
FIG. 4 shows a second view of the pouch and coupler assembly in cross-section.
Figure 5:
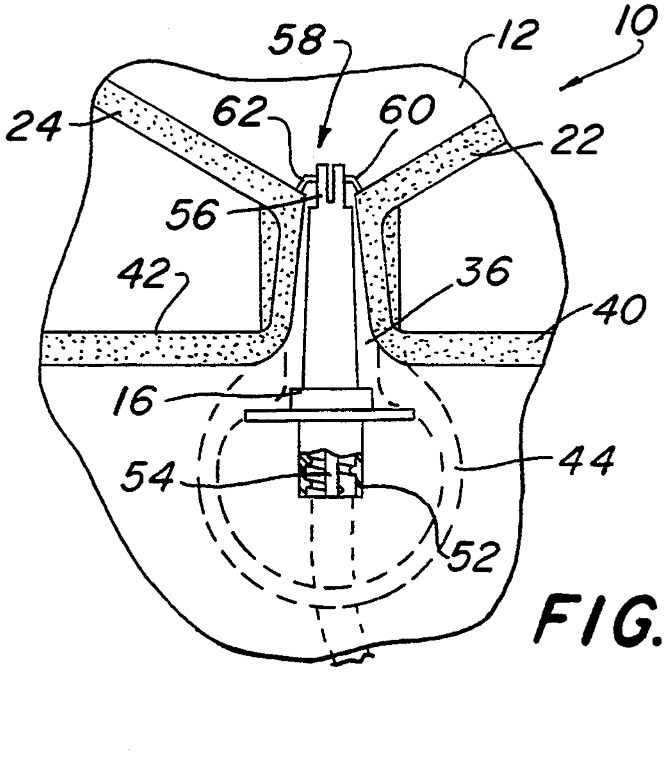
FIG. 5 shows a partial view of the pouch and coupler assembly as taken along line 5—5 in FIG. 4.

In FIGS. 4 and 5, there is shown the pouch 10 in its open condition with the coupler 16 inserted through the peelable seal 38 at the top of channel 36. In FIG. 4, a fluid administration set 50 has been attached to the coupler 16 through the open bottom end 52. In FIG. 5, the open bottom end 52 includes an internal threading which is adapted to be engaged by the threads on the administration set. Also provided is a channel 54 which extends through the center of the coupler 16. A portion of the administration set 50 engages the channel 54 and forms a seal therewith so as to provide fluid access between the coupler 16 and the tubing of the administration set 50. Upon completing this communication, the coupler 16 is projected through the peelable seal 38 into the reservoir 12. In FIGS. 4 and 5, this communication is shown to be made by the projection of end 56 of the coupler 16 through the seal 38. The projected end 56 includes an opening 58 therein which communicates through the coupler 16 to channel 54. Also provided on end 56 are projections 60 and 62 which extend outwardly therefrom. Projections 60 and 62 are intended to be flexible and project a distance greater than the opening through the top end of channel 36. Thus, as illustrated in FIG. 5, when the coupler 16 is projected into the reservoir 12 to engage the angled seams 22 and 24 within the reservoir 12 and to prevent the removal of the coupler 16 from the channel 36. The projections 60, 62 also provide an indication that the pouch 10 has been used previously and is not to be reused.

Figure 6:
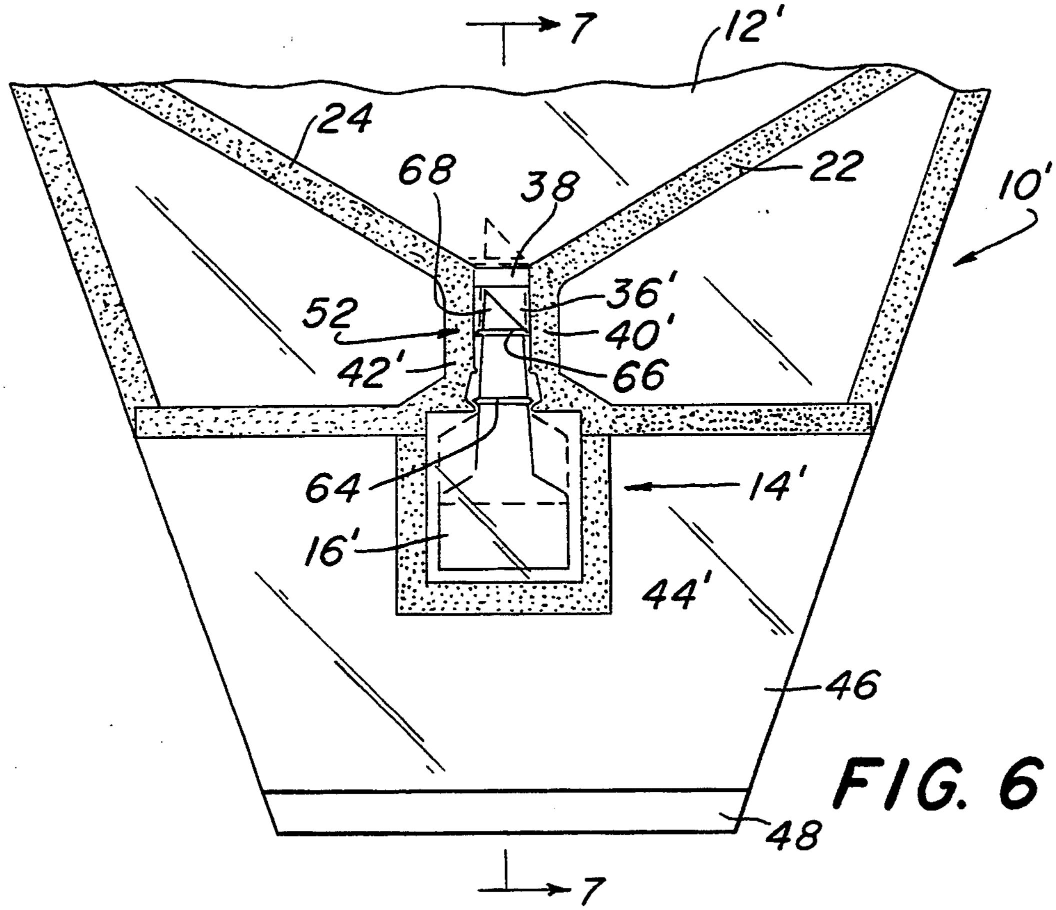
FIG. 6 shows a partial plan view of a portion of an alternate embodiment of the pouch and coupler assembly as contemplated by the present invention.
Figure 7:
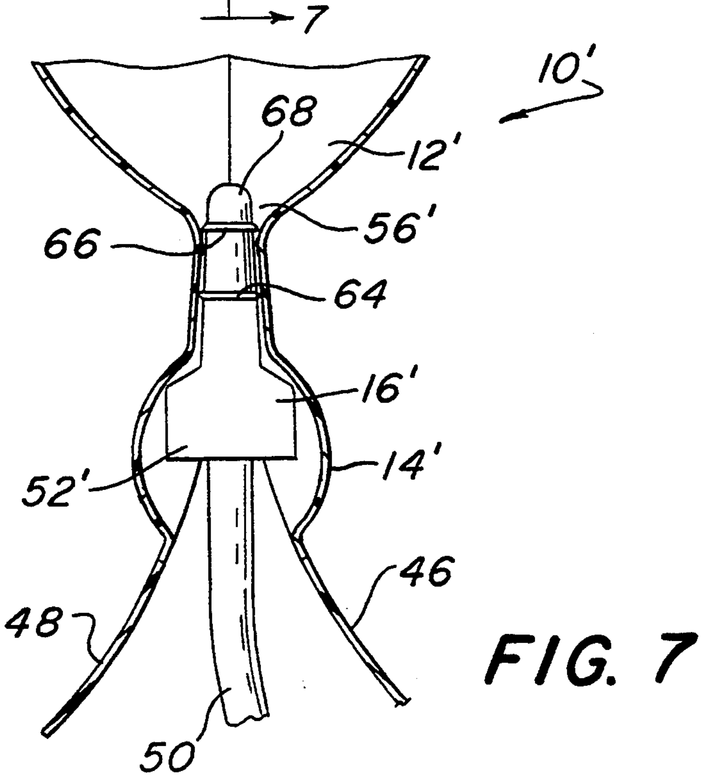
FIG. 7 is a partial cross-sectional view of the embodiment of the pouch and coupler assembly as shown in FIG. 6.

In FIGS. 6 and 7, there is shown another embodiment of a pouch 10′ and coupler 16′ including an alternate channel 36′ and sterile section 14′. In this alternate embodiment as in the prior embodiment, the pouch 10′ includes a coupler 16′ which is maintained within a channel 36′ and is sealed therein upon formation. The upper end of channel 36′ is defined by the peelable seal 38′. Also, a peelable seal 44′ defines the lower end of sterile section 14′ and encapsulates the coupler 16′ within the channel 36′.

Coupler 16′ in FIGS. 6 and 7 includes a bottom end 52′ which is adapted to communicate with a standard fluid administration set 50. The coupler 16′ includes two ridges 64 and 66. The bottom ridge 64 engages within an enlargement of channel 36′ and forms a seal with the opposite side seals 40′ and 42′. The upper ridge 66 also forms a seal with the inside walls of the channel 36′. The channel 36′ is tapered from the peelable seal 38 so as to form a tight engagement. The channel 36′ enlarges somewhat towards its bottom end so as to provide an opening for movement of the bottom ridge 64.

As illustrated in phantom in FIG. 6 and as shown in FIG. 7, end 56′ of the coupler 16′ may be projected through the peelable seal 38 so as to provide fluid communication through the coupler 16′ between the reservoir 12′ and the fluid administration set 50. The projected end 56′ includes an angled projection 68 which is used to open the seal 38. The lower ridge 64 forms a seal with the tapered portion of the upper part of channel 36′. Thus, a fluid seal is formed through the channel 36′. Again, the movement of coupler 16′ within the channel 36′ is intended to form a visual indication of the prior use of the pouch 10′ and to prevent reuse.

In FIGS. 8-12, there is shown a second alternate embodiment of the present invention. In this embodiment, the pouch 10″ includes a coupler 16″ that eliminates the need for a peelable seal at the top of the channel 36″ at the base of the reservoir 12″. The coupler 16″ is again retained within a sterile section 14 having a circular peelable seal 44 formed between opposite projecting tabs 46, 48 and is maintained in a permanent position between the opposite side seals 40″ and 42″ which form the channel 36″. On the outside surface of the upper end of the coupler 16″ is provided a series of ridges 70 which engage the opposite side seals 40″, 42″ of the channel 36″. As particularly illustrated in FIG. 10, the upper end of coupler 16′ has a noncircular cross-section including projecting sides 72 and 74. The opposite side seals 40″ and 42″ are engaged against the ridges 70 and the projected ends 72, 74 so as to form a permanent seal between the reservoir 12″ and the sterile section 14″ as well as to maintain the coupler 16″ in a fixed position.

Figure 8:
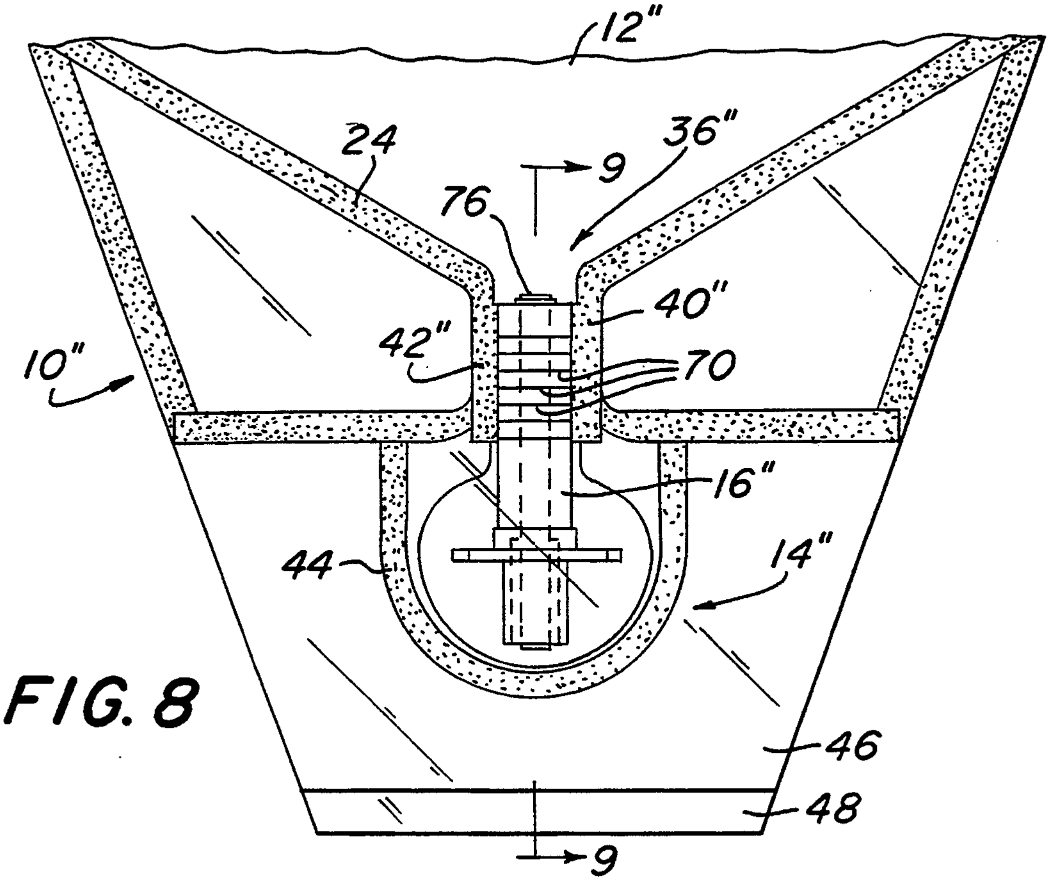
FIG. 8 shows a partial plan view of a second alternate embodiment of the pouch and coupler assembly as contemplated by the present invention.

As illustrated in FIGS. 8 and 9, the coupler 16″ includes a poppet 76 having a top closed end which is sealed within the upper end 78 of the coupler 16″. The poppet 76 includes a longitudinal channel 80 and is essentially hollow. In the upper end 78 of the poppet 76 is provided a crossing channel 82 which extends through the poppet and communicates with channel 80. At the end of poppet 76 opposite from the crossing channel 82 is a receiving end 84 for a fluid administration set 50. The receiving end 84 is defined within the coupler 16″ adjacent to the internal threaded section 86. Adjacent to the receiving end 84 is provided a ridge 88. Ridge 88 is free of the side walls of coupler 16″ in the closed position of the coupler 16″.

Figure 11:
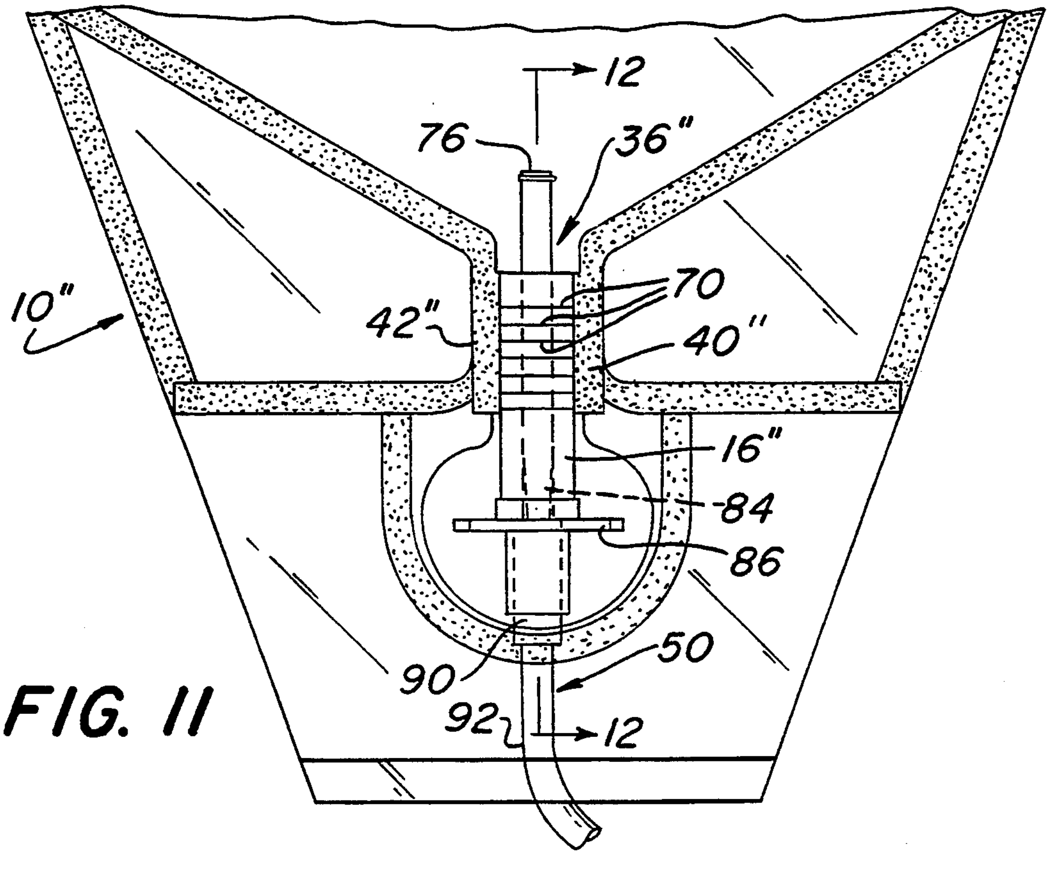
FIG. 11 is a partial plan view of the pouch and coupler assembly in FIG. 8 as shown in the open condition.

In FIGS. 11 and 12, there is shown the coupler 16″ in its open condition. The poppet 76 has been projected upwardly from the upper end 78 of the coupler 16″. Thus, channel 82 is in fluid communication with the reservoir 12″ and fluid may pass through the longitudinal passage 80 into the fluid administration set 50 attached to the coupling end 86 thereof. Administration set 50 includes a threaded end 90 which is secured to a tubing 92. Upon engagement of the threaded end 90 into the internal threaded portion 86, the receiving end 84 seals with the administration set 50 and is pushed upwardly through the central portion of coupler 16″ to project the poppet 76 and to open channel 82. In this projected position of the poppet 76, the ridge 88 seals with the internal walls of coupler 16″.

The embodiment of the coupler 16″ as illustrated provides a visual indication of its having been opened by means of the projection of poppet 76. This feature is consistent with the prior described embodiments. However, the seal of reservoir 12 is formed by the coupler 16″ and poppet 76 rather than by a peelable seal 38 as in the pouches 10 and 10′. In addition, seals 40″ and 42″ engage with ridges 70 to prevent movement of the coupler 16″ within the channel 36″. Thus, the coupler 16″ cannot be removed from the pouch 10″ and the poppet 76 provides a visual indication of it being opened and having been used.

The form of the end 90 of administration set 50 as illustrated in FIGS. 4, 7, 11 and 12 is of the type commonly known as a male luer. Thus, the male connector 90 is inserted into the female end of the coupler (86 in FIG. 12). The present invention is also adaptable to a female luer. Thus, the present invention may be adapted to conform to the practice and custom of the medical industry worldwide and for various uses beyond the medical industry.

The connection between the coupling for the fluid administration set and the coupler of the present invention is contemplated to be made while maintaining the fluid contacting portions in a sterile condition. Although this feature of the invention has particular relevance to the application of administering medical fluids, the advantages obtained thereby have numerous other uses. Moreover, the sterile condition can be maintained without additional packaging for the pouch and/or the coupler portion thereof. First, the connecting end of the coupler 86 (in FIG. 9) is maintained within the sterile section 14″ of the pouch 10″. Secondly, the opening of the sterile section by means of separating the tabs 46, 48 and the peelable seal 44 can be performed without contact of the poppet 76. The opening of the peelable seal can also be performed within a laminar flow hood to further maintain sterile conditions. Next, the hydraulic seal between the administration set (which is typically provided within its own sterile packaging) and the communicating end 84 of the poppet 76 is made prior to the advancement of the poppet into the reservoir 12″ and the passage of fluid through channel 82 and hollow 80. Finally, the poppet 76, having been advanced into the reservoir, provides a visual indication of the prior use of the pouch 10″ and prevents reuse.

It should be apparent that the above noted elements provide substantial advantages for the application of the present invention to numerous types of fluids. The present invention may be embodied in other specific forms without departing from the spirit or essential attributes thereof and, accordingly, reference should be made to the appended claims, rather than to the foregoing specification, as indicating the scope of the invention.

We claim:

1. An apparatus for administering fluids comprising:
a flexible pouch, the pouch having a sealed fluid reservoir and an exhaust channel for the reservoir;
a seal formed between the reservoir and the exhaust channel, coupler means sealed within the exhaust channel of the pouch, and a portion of the pouch formed around the coupler means having a peelable heat seal for releasably enclosing and sealing the coupler means within the pouch, the coupler means being movable within the channel between a first sealed position and a second fluid passage position, the second position permitting fluid passage through the coupler from the reservoir, the opening of the reservoir/exhaust channel seal being created by the movement of at least a portion of the coupler means into the reservoir.

2. An apparatus for administering fluids comprising:
a flexible pouch, the pouch having a sealed fluid reservoir and an exhaust channel for the reservoir;
means forming a seal between the reservoir and the exhaust channel, the seal means comprising coupler means sealed within the exhaust channel of the pouch, the coupler means being moveable within the channel between a first sealed position and a second fluid passage position, the second position permitting fluid passage through the coupler from the reservoir, the opening of the seal being created by the movement of at least a portion of the coupler means and a peelable heat seal formed in the pouch, the seal positioned between the reservoir and the coupler means and the movement of the coupler means causing separation of the peelable seal.

3. An apparatus as claimed in claim 1 or 2, wherein the coupler means further comprises a projected end that moves into the reservoir in the second position.

4. An apparatus as claimed in claim 3, wherein the projected end of the coupler means further comprises an angle portion for breaking the seal when moving from the first position to the second position.

5. An apparatus as claimed in claim 1, wherein the coupler means further comprises a movable poppet means secured within the coupler means, said poppet means forming the seal between the reservoir and the channel with the coupler means within the first position and permitting fluid passage through the coupler from the reservoir in the second position, the opening of the seal being formed by the movement of said poppet means within said coupler.

6. An apparatus as claimed in claim 5, wherein the poppet means further comprises a longitudinal opening extending from one end thereof, a closed end forming the seal with the coupler means in the first position, and a fluid inlet communicating with the longitudinal opening and being in fluid communication with the reservoir when said poppet means is in said second position.

7. An apparatus as claimed in claim 1, wherein the coupler means includes a passageway therethrough and further comprises a poppet having a longitudinal channel extending from one end thereof, a closed end, and a fluid outlet end communicating with said longitudinal channel, the poppet located within the passageway within said coupler and being actuable from a closed position to an open position, such that the closed end of the poppet in the closed position forms a seal between the fluid reservoir means and the longitudinal channel and defines the first position of the coupler means, and in the open position the poppet projects from the coupler, provides access from the reservoir through the longitudinal channel via the fluid outlet end and defines the second position for the couple means.

8. An apparatus as claimed in claims 1, 2, 5 or 7 further comprising connection means for connecting the coupler to a fluid administration element, the connection means forming a hermetic seal with the administration element in the first position of the coupler means.

9. An apparatus as claimed in claim 8 wherein the connection of the fluid administration element to the connection means of the coupler means causes movement of the coupler means from the first position to the second position.

10. An apparatus for administering fluids comprising:

a flexible pouch, the pouch having a sealed fluid reservoir and an exhaust channel for the reservoir;

a coupler sealed within the exhaust channel of the pouch; and poppet means secured with the coupler, said poppet means forming a seal for the channel in a first position and permitting fluid passage through the coupler from the reservoir in a second position, the opening of the seal being formed by the movement of the said poppet means within said coupler.

11. An apparatus for administering fluids comprising:

a flexible pouch, the pouch having a sealed fluid reservoir and an exhaust channel for the reservoir;

a coupler sealed with the exhaust channel of the pouch; and poppet means secured within the coupler, said poppet means forming a seal for the channel within a first position and permitting fluid passage through the coupler from the reservoir in a second position, the opening of the seal being formed by the movement of the said poppet means within said coupler, fluid administration means having an attachment means for releasably attaching to the coupler means, the attachment of the attachment means to the coupler means causing the movement of the coupler means from the first position to the second position.

12. An apparatus as claimed in claim 10 or 11, wherein said poppet means includes a longitudinal opening extending from one end thereof, a closed end forming the seal with the coupler in the first position, and a fluid inlet communicating with the longitudinal opening and being in fluid communication with the reservoir when said poppet means is in said second position.

13. An apparatus for administering fluids comprising:

a pouch forming a fluid reservoir, said pouch having an exhaust channel therein; coupler means sealed within the channel, said coupler means having a passageway therethrough, a portion of the pouch formed around the coupler means and having a peelable heat seal for releasably enclosing and sealing the coupler means within the pouch;

and a poppet having a longitudinal channel extending from one end thereof, a closed end, and a fluid outlet end communicating with said longitudinal channel, the poppet located within the passageway within said coupler means and being actuable from a closed position to an open position, such that the closed end of the poppet in the closed position forms a seal between the fluid reservoir and the longitudinal channel of the poppet, and in the open position the poppet projects from the coupler into the reservoir and provides access from the reservoir through the longitudinal channel via the fluid outlet end.

14. An apparatus for administering fluids comprising:

a sealed fluid reservoir, said reservoir having an exhaust channel therein; a coupler means sealed within the channel, said coupler means having a passageway therethrough;

a poppet having a longitudinal channel extending from one end thereof, a closed end, and a fluid outlet end communicating with said longitudinal channel, the poppet located within the passageway within said coupler means and being actuable from a closed position to an open position, such that the closed end of the poppet in the closed position forms a seal between the fluid reservoir and the longitudinal channel of the poppet, and in the open position the poppet projects from the coupler into the reservoir and provides access from the reservoir through the longitudinal channel via the fluid outlet end;

and fluid administration means, said administration means having attachment means for releasably attaching to the coupler means, the attachment of the attachment means to the coupler means causing the movement of the poppet from the closed position to the open position.

15. An apparatus as claimed in claim 13 further comprising connection means for connecting the coupler to a fluid administration element, the connection means forming a hermetic seal between the poppet and the administration element in the closed position.

16. An apparatus as claimed in claim 15 wherein the connection of the fluid administration means to the connection means of the couple means causes movement of the poppet from the closed position to the open position.

17. An apparatus as claimed in claim 13 wherein the coupler means forms a female connection adapted to receive a fluid administration element having a male luer thereon.

18. An apparatus for administering fluids comprising:

a flexible pouch, the pouch having a sealed fluid reservoir and exhaust channel for the reservoir;

means forming a seal between the reservoir and the exhaust channel, the seal means comprising coupler means sealed within the exhaust channel of the pouch, the coupler means being moveable within the channel between a first sealed position and a second fluid passage position, and the coupler means having a projected end that moves into the reservoir in the second position permitting fluid passage through the coupler from the reservoir, the opening of the seal being created by the movement of at least a portion of the coupler means and the projected end of the coupler means having projecting tabs that extend transversely into the reservoir in the second position beyond the opening of the exhaust channel.

19. An apparatus as claimed in claim 18 wherein the seal means further comprises a peelable heat seal formed in the pouch, the seal positioned between the reservoir and the coupler means and the movement of the coupler means causing separation of the peelable seal.

* * * * *